US00PP31527P3

(12) United States Plant Patent
Carrillo Mendoza et al.

(10) Patent No.: US PP31,527 P3
(45) Date of Patent: Mar. 10, 2020

(54) STRAWBERRY PLANT VARIETY NAMED 'DRISSTRAWSIXTYTWO'

(50) Latin Name: ***Fragaria* x *ananassa***
Varietal Denomination: DrisStrawSixtyTwo

(71) Applicant: Driscoll's, Inc., Watsonville, CA (US)

(72) Inventors: Omar Carrillo Mendoza, La Calera (MX); Luis Miguel Rodriguez, Watsonville, CA (US); Michael D. Ferguson, Moorpark, CA (US); Philip J. Stewart, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 15/998,170

(22) Filed: Jul. 12, 2018

(65) Prior Publication Data

US 2020/0022294 P1 Jan. 16, 2020

(51) Int. Cl.
*A01H 5/08* (2018.01)
*A01H 6/74* (2018.01)

(52) U.S. Cl.
USPC ..... Plt./208
CPC ..... *A01H 6/74* (2018.05)

(58) Field of Classification Search
USPC ..... Plt./208, 209
CPC ..... A01H 5/0893
See application file for complete search history.

(56) References Cited

U.S. PATENT DOCUMENTS

PP1,745 P 8/1958 Lang
PP3,981 P 11/1976 Bringhurst et al.
PP4,487 P 11/1979 Bringhurst et al.
PP4,538 P 5/1980 Bringhurst et al.
PP5,262 P 7/1984 Voth et al.
PP5,265 P 7/1984 Voth et al.
PP5,266 P 7/1984 Bringhurst et al.
PP5,300 P 10/1984 Johnson Jr.
PP5,480 P 5/1985 Nakagawa
PP5,840 P 12/1986 Johnson, Jr. et al.
PP6,191 P 5/1988 Johnson, Jr. et al.
PP6,231 P 7/1988 Johnson, Jr. et al.
PP6,578 P 1/1989 Voth et al.
PP6,579 P 1/1989 Bringhurst et al.
PP7,024 P 9/1989 Johnson, Jr. et al.
PP7,172 P 2/1990 Voth et al.
PP7,522 P 5/1991 Johnson, Jr. et al.
PP7,614 P 8/1991 Bringhurst et al.
PP7,615 P 8/1991 Bringhurst et al.
PP8,086 P 1/1993 Nelson et al.
PP8,205 P 4/1993 Nelson et al.
PP8,649 P 3/1994 Sjulin et al.
PP8,661 P 3/1994 Bringhurst et al.
PP8,708 P 5/1994 Voth et al.
PP8,745 P 5/1994 Sjulin et al.
PP9,130 P 5/1995 Sjulin et al.
PP9,909 P 6/1997 Ackerman et al.
PP10,221 P 2/1998 Sjulin et al.
PP10,534 P 8/1998 Sjulin et al.
PP10,642 P 10/1998 Amorao et al.
PP11,035 P 8/1999 Mowrey et al.
PP11,277 P 3/2000 Gilford et al.
PP11,279 P 3/2000 Gilford et al.
PP11,522 P 9/2000 Amorao et al.
PP11,548 P 10/2000 Amorao et al.
PP11,554 P 10/2000 Sjulin et al.
PP11,639 P 11/2000 Mowrey et al.
PP12,186 P2 11/2001 Gilford et al.
PP12,436 P2 3/2002 Amorao et al.
PP12,577 P2 4/2002 Amorao et al.
PP12,817 P2 7/2002 Gilford et al.
PP12,889 P2 8/2002 Lamb et al.
PP12,899 P2 9/2002 Mowrey et al.
PP13,386 P2 12/2002 Mowrey et al.
PP13,469 P3 1/2003 Larson et al.
PP14,005 P3 7/2003 Amorao et al.
PP14,062 P3 8/2003 Amorao et al.
PP14,109 P3 8/2003 Gilford et al.
PP14,771 P3 5/2004 Amorao et al.
PP15,145 P2 9/2004 Mowrey et al.
PP15,308 P2 11/2004 Sjulin et al.
PP15,375 P2 11/2004 Mowrey et al.
PP15,435 P2 12/2004 Sjulin et al.
PP15,596 P2 3/2005 Amorao et al.
PP15,731 P2 4/2005 Amorao et al.
PP15,752 P2 5/2005 Gilford et al.
PP16,070 P2 10/2005 Gilford et al.
PP16,238 P2 2/2006 Amorao et al.
PP16,241 P2 2/2006 Mowrey et al.
PP16,298 P2 2/2006 Gilford et al.
PP16,299 P2 2/2006 Gilford et al.
PP16,475 P2 4/2006 Gilford et al.
PP16,558 P3 5/2006 López
PP18,000 P2 9/2007 Meulenbroek
PP18,040 P3 9/2007 Mowrey et al.
PP18,041 P3 9/2007 Gilford
PP18,458 P2 1/2008 Ferguson et al.
PP18,575 P3 3/2008 Amorao et al.
PP18,878 P2 6/2008 Mowrey et al.
PP19,240 P2 9/2008 Gilford et al.
PP19,673 P3 2/2009 Ferguson et al.
PP19,767 P2 2/2009 Shaw et al.
PP20,248 P3 9/2009 Rogers et al.
PP20,701 P2 2/2010 Gilford et al.
PP20,731 P2 2/2010 Mowrey et al.
PP20,733 P2 2/2010 Mowrey et al.
PP20,735 P2 2/2010 Ferguson
PP20,775 P2 2/2010 Mowrey et al.
PP20,922 P2 4/2010 Gilford et al.
PP21,538 P2 11/2010 Gilford et al.
PP21,559 P2 12/2010 Ferguson et al.
PP21,762 P2 3/2011 Stewart et al.
PP22,040 P3 7/2011 Stewart et al.
PP22,218 P2 11/2011 Ferguson
PP22,247 P2 11/2011 Ferguson
PP23,107 P2 10/2012 Ferguson et al.
PP23,148 P2 10/2012 Gilford et al.

(Continued)

OTHER PUBLICATIONS

Fear et al., Unpublished U.S. Appl. No. 15/998,014, filed Jun. 11, 2018, titled "Strawberry Plant Variety Named 'DrisStrawFiftyEight'".

(Continued)

*Primary Examiner* — Kent L Bell
(74) *Attorney, Agent, or Firm* — Morrison & Foerster LLP

(57) ABSTRACT

A new and distinct variety of strawberry plant named 'DrisStrawSixtyTwo', particularly characterized by its yield potential, fruit size and flavor, and shelf-life, is disclosed.

4 Drawing Sheets

(56) References Cited

U.S. PATENT DOCUMENTS

| | | | |
|---|---|---|---|
| PP23,377 | P2 | 2/2013 | Ferguson et al. |
| PP23,378 | P2 | 2/2013 | Pullen et al. |
| PP23,382 | P2 | 2/2013 | Ferguson et al. |
| PP23,383 | P2 | 2/2013 | Ferguson et al. |
| PP23,400 | P2 | 2/2013 | Ferguson et al. |
| PP23,401 | P2 | 2/2013 | Pullen et al. |
| PP23,459 | P2 | 3/2013 | Stewart et al. |
| PP23,506 | P3 | 4/2013 | Ferguson et al. |
| PP23,517 | P3 | 4/2013 | Ferguson et al. |
| PP24,096 | P3 | 12/2013 | Fear et al. |
| PP24,317 | P3 | 3/2014 | Ferguson et al. |
| PP24,333 | P3 | 3/2014 | Vitten et al. |
| PP24,395 | P3 | 4/2014 | Vitten et al. |
| PP24,533 | P3 | 6/2014 | Ferguson et al. |
| PP24,745 | P2 | 8/2014 | Vitten et al. |
| PP25,408 | P3 | 4/2015 | Vitten et al. |
| PP25,437 | P3 | 4/2015 | Vitten et al. |
| PP25,698 | P3 | 7/2015 | Ferguson et al. |
| PP25,699 | P3 | 7/2015 | Stewart et al. |
| PP25,747 | P3 | 7/2015 | Kibbe et al. |
| PP25,866 | P3 | 9/2015 | Ferguson et al. |
| PP26,800 | P3 | 6/2016 | Stewart et al. |
| PP26,801 | P3 | 6/2016 | Stewart et al. |
| PP26,802 | P3 | 6/2016 | Rodriguez Alcazar et al. |
| PP27,442 | P2 | 12/2016 | Kibbe et al. |
| PP27,645 | P3 | 2/2017 | Vitten et al. |
| PP27,682 | P3 | 2/2017 | Kibbe et al. |
| PP27,711 | P3 | 2/2017 | Vitten et al. |
| PP27,813 | P3 | 3/2017 | Ferguson et al. |
| PP29,289 | P3 | 5/2018 | Vitten et al. |
| 2003/0079263 | P1 | 4/2003 | Gilford et al. |
| 2013/0276182 | P1 | 10/2013 | Fear et al. |

OTHER PUBLICATIONS

Ferguson et al., Unpublished U.S. Appl. No. 15/731,546, filed Jun. 26, 2017, titled "Strawberry Plant Variety Named 'DrisStrawFiftySix'".

Kibbe et al., Unpublished U.S. Appl. No. 15/731,542, filed Jun. 26, 2017, titled "Strawberry Plant Variety Named 'DrisStrawFiftyTwo'".

Kibbe et al., Unpublished U.S. Appl. No. 15/731,545, filed Jun. 26, 2017, titled "Strawberry Plant Variety Named 'DrisStrawFiftyOne'".

Mendoza, et al., Unpublished U.S. Appl. No. 15/998,020, filed Jun. 12, 2018, titled "Strawberry Plant Variety Named 'DrisStrawSixtyOne'".

Mendoza, et al., Unpublished U.S. Appl. No. 15/998,169, filed Jul. 12, 2018, titled "Strawberry Plant Variety Named 'DrisStrawSixtyThree'".

Pakozdi et al., Unpublished U.S. Appl. No. 15/998,015, filed Jun. 11, 2018, titled "Strawberry Plant Variety Named 'DrisStrawFiftyNine'".

Pakozdi et al., Unpublished U.S. Appl. No. 15/998,028, filed Jun. 14, 2018, titled "Strawberry Plant Variety Named 'DrisStrawSixtyFive'".

Stewart et al., Unpublished U.S. Appl.. No. 15/731,415, filed Jun. 6, 2017, titled "Strawberry Plant Variety Named 'DrisStrawFiftyThree'".

Stewart et al., Unpublished U.S. Appl. No. 15/731,421, filed Jun. 6, 2017, titled "Strawberry Plant Variety Named 'DrisStrawFiftySeven'".

Stewart et al., Unpublished U.S. Appl. No. 15/998,031, filed Jun. 14, 2018, titled "Strawberry Plant Variety Named 'DrisStrawSixtyFour'".

Vitten et al., Unpublished U.S. Appl. No. 15/731,559, filed Jun. 27, 2017, titled "Strawberry Plant Variety Named 'DrisStrawFiftyFour'".

Vitten et al., Unpublished U.S. Appl. No. 15/731,560, filed Jun. 27, 2017, titled "Strawberry Plant Variety Named 'DrisStrawFiftyFive'".

STRAWBERRY PLANT VARIETY NAMED 'DRISSTRAWSIXTYTWO'

Latin name: Botanical classification: *Fragaria* x *ananassa*.

Varietal denomination: The varietal denomination of the claimed variety of strawberry plant is 'DrisStrawSixtyTwo'.

BACKGROUND OF THE INVENTION

Cultivated strawberry is a hybrid species of the genus *Fragaria* that is grown worldwide for its fruit. Modern strawberry was first bred in Brittany, France, in the 18$^{th}$ century by crossing *Fragaria virginiana* with *Fragaria chiloensis*. Strawberry fruit is an aggregate accessory fruit, with the fleshy part of the fruit being derived from the receptacle that holds the ovaries.

Strawberry varieties vary widely in color, size, shape, flavor, season of ripening, degree of fertility, and susceptibility to disease. Certain varieties vary in foliage, and some vary in the relative development of their reproductive organs. Typically, strawberry flowers appear hermaphroditic in structure, but function as either male or female. Generally, commercial production of strawberry plants involves propagation from runners and distribution as either plugs or bare root plants. Cultivation is either perennial or annual plasticulture. During the off season, strawberries can also be produced in greenhouses.

Strawberry fruit is widely appreciated for its characteristic bright red color, aroma, juicy texture, and sweetness. Strawberry fruit is a popular fruit that is generally consumed either fresh or in prepared foods, such as preserves and baked goods.

Strawberry is an important and valuable fruit crop. Accordingly, there is a need for new varieties of strawberry plants. In particular, there is a need for improved varieties of strawberry plant that are stable, high yielding, and agronomically sound.

SUMMARY OF THE INVENTION

In order to meet these needs, the present invention is directed to an improved variety of strawberry plant. In particular, the invention relates to a new and distinct variety of strawberry plant (*Fragaria* x *ananassa*), which has been denominated as 'DrisStrawSixtyTwo'.

Strawberry plant variety 'DrisStrawSixtyTwo' was selected in Tapalpa, Mexico in October of 2012, and originated from a cross between the proprietary female parent '73P176' (unpatented) and the proprietary male parent '107P249' (unpatented). A single plant was selected and asexually propagated via stolons in Tapalpa, Mexico.

'DrisStrawSixtyTwo' was subsequently asexually propagated via stolons, and underwent testing at a farm in Tapalpa, Mexico for six years. The present variety has been found to be stable and reproduce true to type through successive asexual propagations via stolons.

'DrisStrawSixtyTwo' exhibits the following distinguishing characteristics over other similar varieties when grown under normal horticultural practices in Tapalpa, Mexico:

1. Higher yield;
2. Bearing that is partially remontant;
3. Stronger plant vigor; and
4. Larger fruit with sweet flavor.

'DrisStrawSixtyTwo' was selected for its yield potential, fruit size and flavor, and shelf-life.

DESCRIPTION OF THE DRAWINGS

This new strawberry plant is illustrated by the accompanying photographs which show fruit, flowers, and leaves of the plant. The colors shown are as true as can be reasonably obtained by conventional photographic procedures. The photographs are of plants that are six months old.

DESCRIPTION OF THE NEW VARIETY

Figure 1:
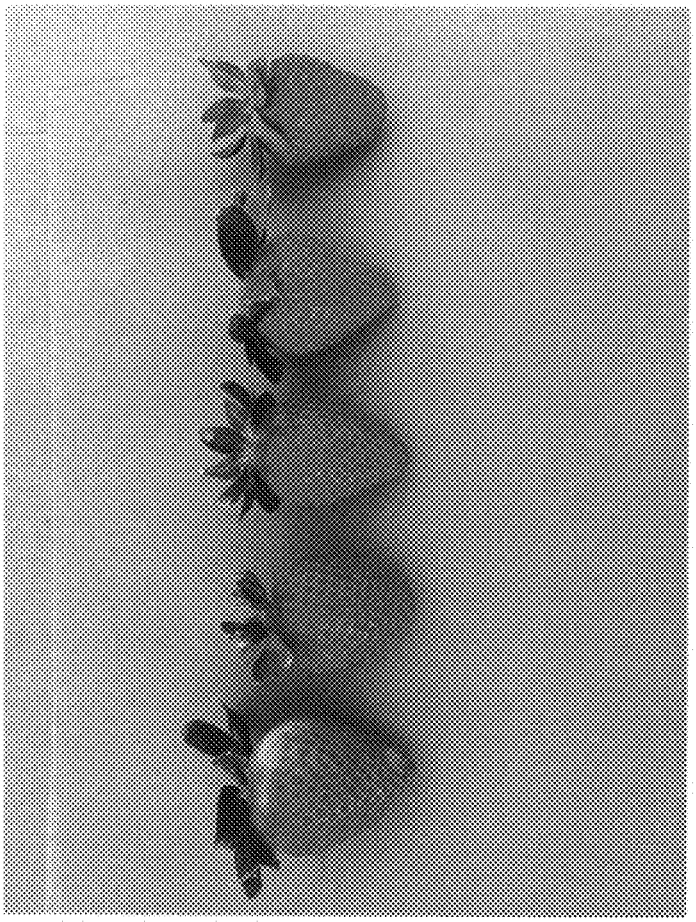
FIG. 1 illustrates whole fruit of variety 'DrisStrawSixtyTwo'.
Figure 2:
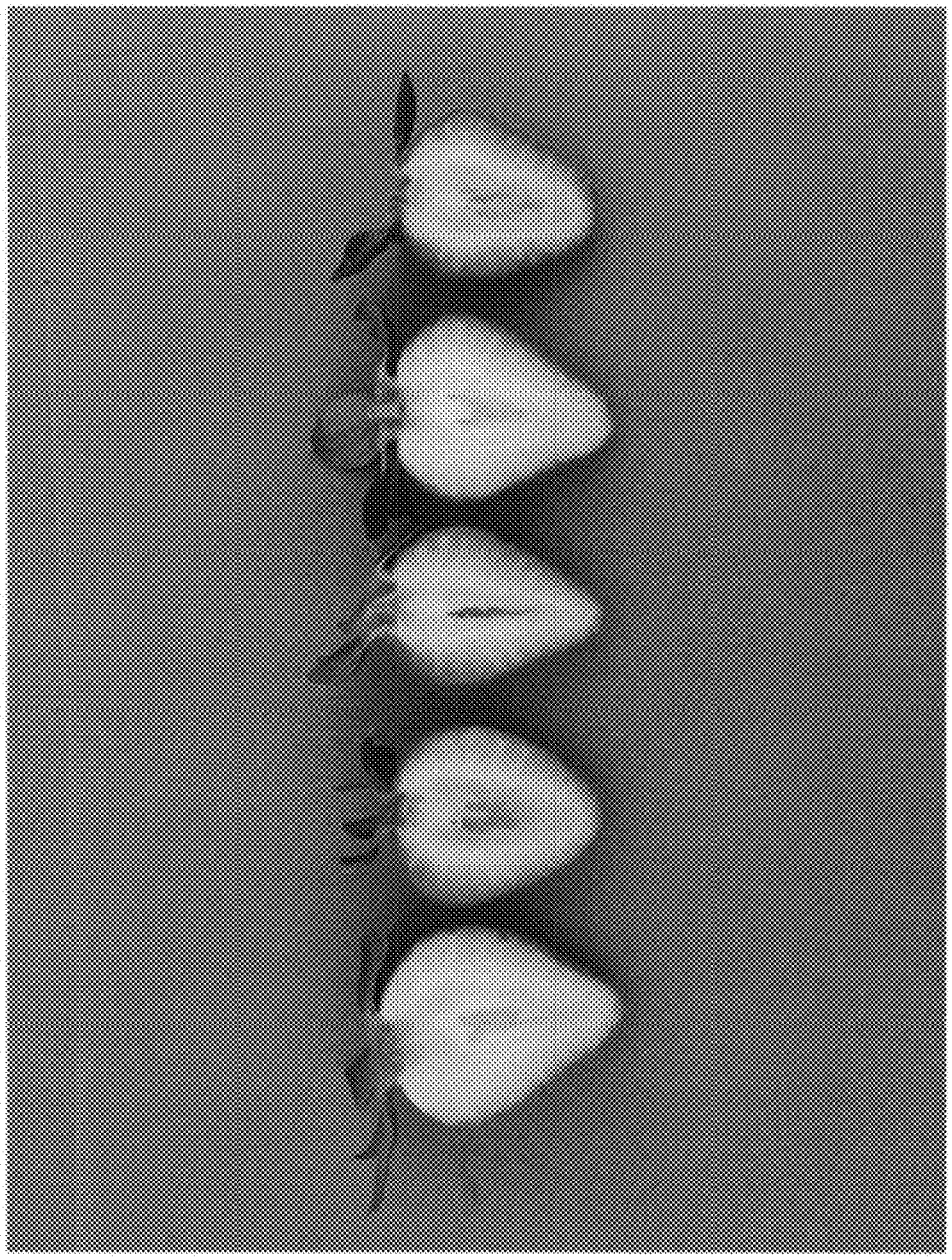
FIG. 2 illustrates longitudinal cross-sections of fruit of variety 'DrisStrawSixtyTwo'.
Figure 3:
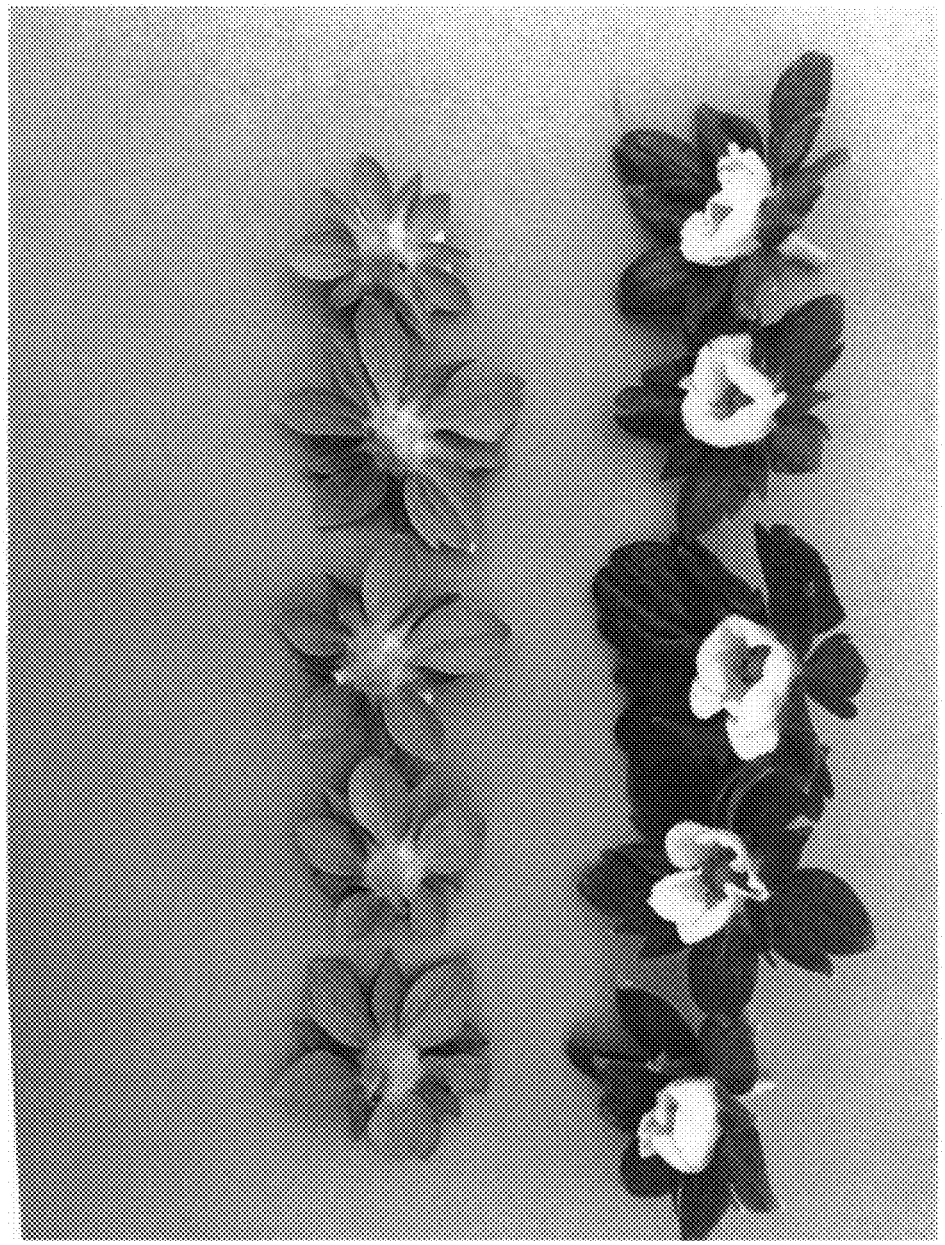
FIG. 3 illustrates both the upper and lower surfaces of flowers of variety 'DrisStrawSixtyTwo'.
Figures 4A, 4B:
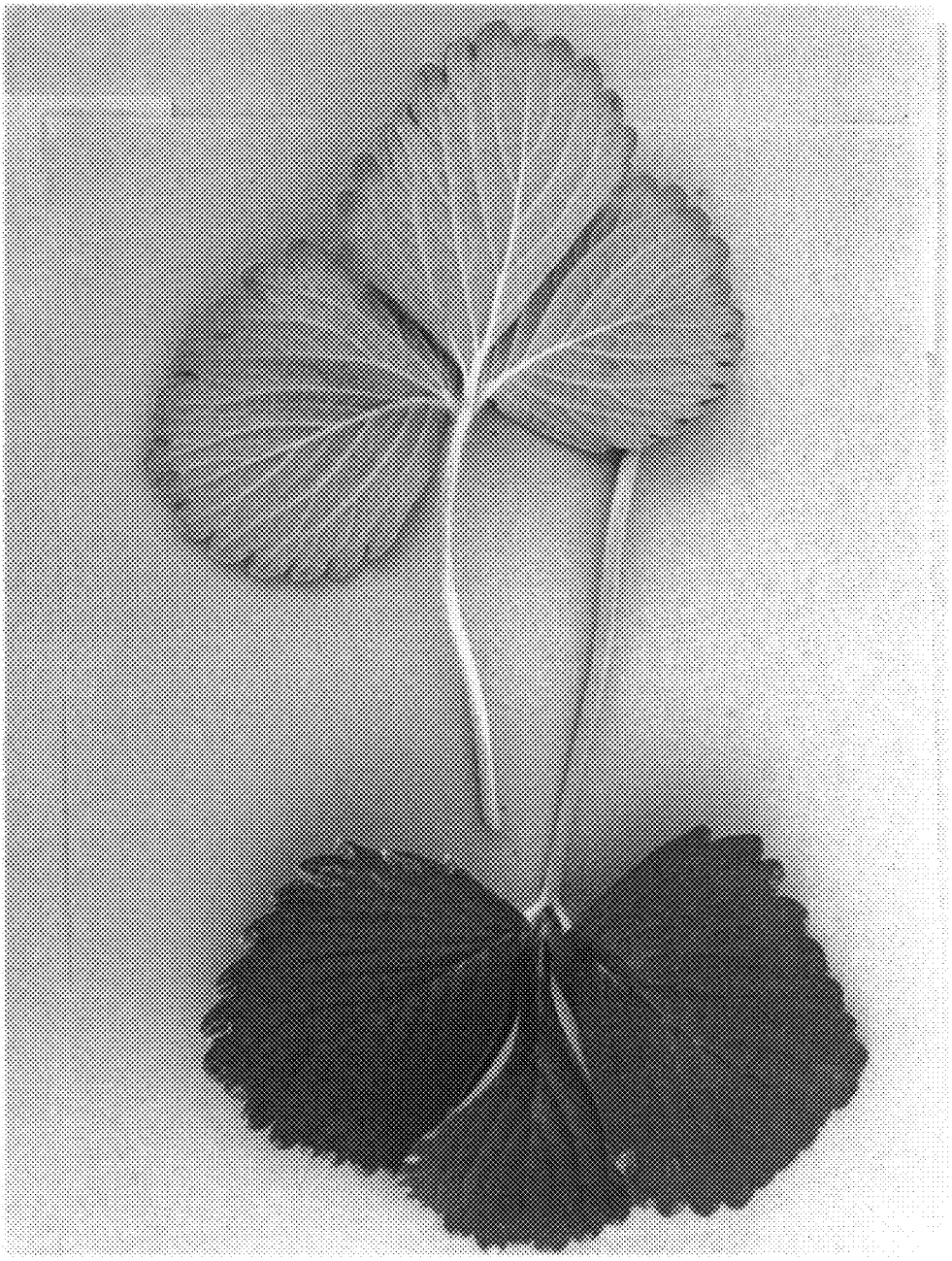
FIG. 4A illustrates the upper surface of a leaf of variety 'DrisStrawSixtyTwo'.
FIG. 4B illustrates the lower surface of a leaf of variety 'DrisStrawSixtyTwo'.

The following detailed descriptions set forth the distinctive characteristics of 'DrisStrawSixtyTwo'. The data which define these characteristics is based on observations taken in Tapalpa, Mexico for six years. This description is in accordance with UPOV terminology. Color designations, color descriptions, and other phenotypical descriptions may deviate from the stated values and descriptions depending upon variation in environmental, seasonal, climatic, and cultural conditions. 'DrisStrawSixtyTwo' has not been observed under all possible environmental conditions. The botanical description of 'DrisStrawSixtyTwo' was taken from plants that were six months old. The indicated values represent averages calculated from measurements of several plants. Color references are primarily to The RHS Colour Chart of The Royal Horticultural Society of London (RHS) (2007 edition). Descriptive terminology follows the Plant Identification Terminology, An Illustrated Glossary, 2$^{nd}$ edition by James G. Harris and Melinda Woolf Harris, unless where otherwise defined.

DETAILED BOTANICAL DESCRIPTION OF THE PLANT

Classification:
- *Species.*—*Fragaria* x *ananassa*.
- *Common name.*—Strawberry.
- *Denomination.*—'DrisStrawSixtyTwo'.

Parentage:
- *Female parent.*—The proprietary variety '73P176' (unpatented).
- *Male parent.*—The proprietary variety '107P249' (unpatented).

Plant:
- *Height.*—23.7 cm.
- *Diameter.*—35.9 cm.
- *Number of crowns/plant.*—6.
- *Growth habit.*—Spreading.

Stolon:
- *Average number of daughter plants per square foot.*—17.
- *Diameter at bract.*—3.16 mm.
- *Anthocyanin coloration.*—Present.
- *Anthocyanin color.*—RHS 52A (Vivid red).

Leaf:
- *Number of leaflets.*—Three only.
- *Color of upper surface.*—RHS 137A (Moderate olive green).
- *Color of lower surface.*—RHS 138A (Moderate yellowish green).
- *Variegation.*—Absent.

*Terminal Leaflets.*—Length: 10.1 cm. Width: 10.2 cm. Length/width ratio: 1.0. Number of teeth/terminal leaflet: 22. Leaflet shape: Obicular. Shape of apex: Rounded. Shape of base: Obtuse. Margin: Crenate. Shape in cross section: Concave.

*Petiole.*—Length: 16.0 cm. Diameter: 5.40 mm. Color: RHS 145B (Light yellow green). Attitude of hairs: Horizontal. Bract frequency (number present on each petiole): 2.

*Petiolule.*—Length: 10.10 mm. Diameter: 3.10 mm. Color: RHS 145C (Light yellow green).

*Stipule.*—Length: 3.3 cm. Width: 19.03 mm. Anthocyanin coloration: Absent.

Inflorescence:

*Position in relation to foliage.*—Same level.

*Pedicel.*—Length: 12 cm. Diameter: 3 mm. Color: RHS 145C (Light yellow green). Attitude of hairs: Horizontal.

*Flower.*—Flower diameter (petal tip to petal tip on non-flattened flower): 24.00 mm. Flower depth: 15 mm. Arrangement of petals: Overlapping. Stamen: Present. Typical and observed number of flowers per plant: 17.10.

*Petal.*—Length: 14.90 mm. Width: 13.60 mm. Length/width ratio: 1.1. Petal shape: Orbicular. Shape of apex: Rounded. Shape of base: Concavo-convex. Margin: Entire. Typical and observed petal number: 6. Color of upper surface: RHS 155B (Yellowish white). Color of lower surface: RHS 155C (Greenish white).

*Calyx.*—Diameter (sepal tip to sepal tip, measured on back of flower): 45.70 mm.

*Sepal.*—Length (sepal tip to point of attachment to receptacle): 23.60 mm. Width: 16.80 mm. Color of upper surface: RHS 139A (Dark yellowish green). Color of lower surface: RHS 144A (Strong yellowish green). Sepal shape: Elliptical. Shape of apex: Truncate. Margin: Entire. Typical and observed sepal number: 10.

Fruit:

*Length.*—57.30 mm.

*Width.*—42.50 mm.

*Weight (individual fruit).*—27 g.

*Length/width ratio.*—1.3.

*Fruit hollow length.*—27.20 mm.

*Fruit hollow width.*—10.00 mm.

*Fruit hollow length/width ratio.*—2.7.

*Shape.*—Cylindrical.

*Color.*—RHS 180A (Moderate red).

*Position of achenes.*—Level with surface.

*Color of achenes.*—RHS 1A (Brilliant greenish yellow).

*Position of calyx attachment.*—Level with fruit.

*Attitude of sepals.*—Upwards.

*Color of flesh (excluding core).*—RHS 39A (Strong red).

*Color of core.*—RHS 48B (Deep pink).

*Fruiting truss.*—Length: 29 cm. Diameter: 5 mm. Color: RHS 145A (Strong yellow green). Number of berries per truss: 7 berries.

Production:

*Flowering interval.*—October to April.

*Harvest interval.*—October to April.

*Type of bearing.*—Partially everbearing to partially remontant.

*Productivity.*—27806 kg to 36767 kg of fruit per hectare per season from six-month-old plants when grown in Tapalpa, Mexico.

Resistance to abiotic stress, pests and diseases:

*Waterlogging.*—Moderately susceptible.

*Two-spotted spider mite (Tetranychus urticae).*—Susceptible.

*Botrytis fruit rot (Botrytis cinerea).*—Moderately resistant.

*Powdery mildew (Podosphaera macularis).*—Moderately resistant.

*Xanthomonas fragariae.*—Moderately susceptible.

COMPARISON WITH PARENTAL AND COMMERCIAL VARIETIES

'DrisStrawSixtyTwo' differs from the proprietary female parent '73P176' (unpatented) in that 'DrisStrawSixtyTwo' has a bearing that is partially remontant, whereas '73P176' is a short day variety. Moreover, fruit of 'DrisStrawSixtyTwo' have a sweeter flavor and are less firm than fruit of '73P176'.

'DrisStrawSixtyTwo' differs from the proprietary male parent '107P249' (unpatented) in that plants of 'DrisStrawSixtyTwo' have a stronger vigor and produce higher yields of fruit than plants of '107P249'. Moreover, fruit of 'DrisStrawSixtyTwo' are larger in size with a less sweet taste than fruit of '107P249'.

'DrisStrawSixtyTwo' differs from the commercial variety 'DrisStrawTwentySeven' (U.S. Plant Pat. No. 23,400) in that plants of 'DrisStrawSixtyTwo' have absent or weak leaf blistering, while plants of 'DrisStrawTwentySeven' have medium leaf blistering. Additionally, plants of 'DrisStrawSixtyTwo' have large flowers that are positioned level with foliage, while plants of 'DrisStrawTwentySeven' have medium flowers that are positioned above foliage. Moreover, 'DrisStrawSixtyTwo' has a terminal leaflet margin that is crenate, a fruit shape that is cylindrical, position of achenes that is level with surface of fruit, a medium width of band without achenes, position of calyx attachment that is level with fruit, and is moderately resistant to botrytis fruit rot and *Xanthomonas fragariae*; whereas 'DrisStrawTwentySeven' has a terminal leaflet margin that is serrate, a fruit shape that is conical, position of achenes that is below surface of fruit, a very broad width of band without achenes, position of calyx attachment that is above fruit, is susceptible to botrytis fruit rot, and is moderately susceptible to powdery mildew.

'DrisStrawSixtyTwo' differs from the commercial variety 'Driscoll El Dorado' (U.S. Plant Pat. No. 16,238) in that 'DrisStrawSixtyTwo' has a spreading growth habit and medium dense foliage, while 'Driscoll El Dorado' has a semi-upright growth habit and dense foliage. Additionally, leaves of 'DrisStrawSixtyTwo' have absent or weak leaf blistering, while leaves of 'Driscoll El Dorado' have strong leaf blistering. Moreover, 'DrisStrawSixtyTwo' has a terminal leaflet base that is obtuse in shape, hairs on petiole that have an attitude that is horizontal, fruit that is cylindrical in shape, position of achenes that is level with surface of fruit, and is moderately resistant to botrytis fruit rot; while 'Driscoll El Dorado' has a terminal leaflet base that is rounded in shape, hairs on petiole that have an attitude that is upwards to outwards, fruit that is conical in shape, position of achenes that is below the surface of fruit, and is susceptible to botrytis fruit rot.

We claim:

1. A new and distinct variety of strawberry plant named 'DrisStrawSixtyTwo' as shown and described herein.

* * * * *